United States Patent [19]

Solomon et al.

[11] 4,004,430
[45] Jan. 25, 1977

[54] PROCESS AND APPARATUS FOR TREATING NATURAL GAS

[75] Inventors: Stephen M. Solomon, New York, N.Y.; Sidney Shaievitz, Livingston, N.J.; Louis Marshall, Great Neck, N.Y.

[73] Assignee: The Lummus Company, Bloomfield, N.J.

[22] Filed: Sept. 30, 1974

[21] Appl. No.: 510,367

[52] U.S. Cl. .................................. 62/18; 62/26; 62/28; 62/38
[51] Int. Cl.² ................................... F25J 3/00
[58] Field of Search .............. 62/9, 11, 32, 34, 36, 62/38, 40, 41, 42, 23, 24, 26, 31, 44, 28, 18

[56] References Cited
UNITED STATES PATENTS

| | | | |
|---|---|---|---|
| 3,213,631 | 10/1965 | Kniel | 62/40 |
| 3,312,073 | 4/1967 | Jackson et al. | 62/38 |
| 3,837,172 | 9/1974 | Markbreiter et al. | 62/38 |

*Primary Examiner*—Frank W. Lutter
*Assistant Examiner*—Frank Sever
*Attorney, Agent, or Firm*—Marn & Jangarathis

[57] ABSTRACT

There is disclosed a process and apparatus for recovering ethane and heavier hydrocarbons from natural gas by heating the natural gas stream prior to the expansion and introduction thereof into a demethanizer operating under cryogenic conditions. Ethane and the heavier hydrocarbons are recovered from the demethanizer as well as a residual gaseous methane stream which is compressed to a pipeline receiving pressure by the work of expansion without requiring a booster compressor.

10 Claims, 1 Drawing Figure

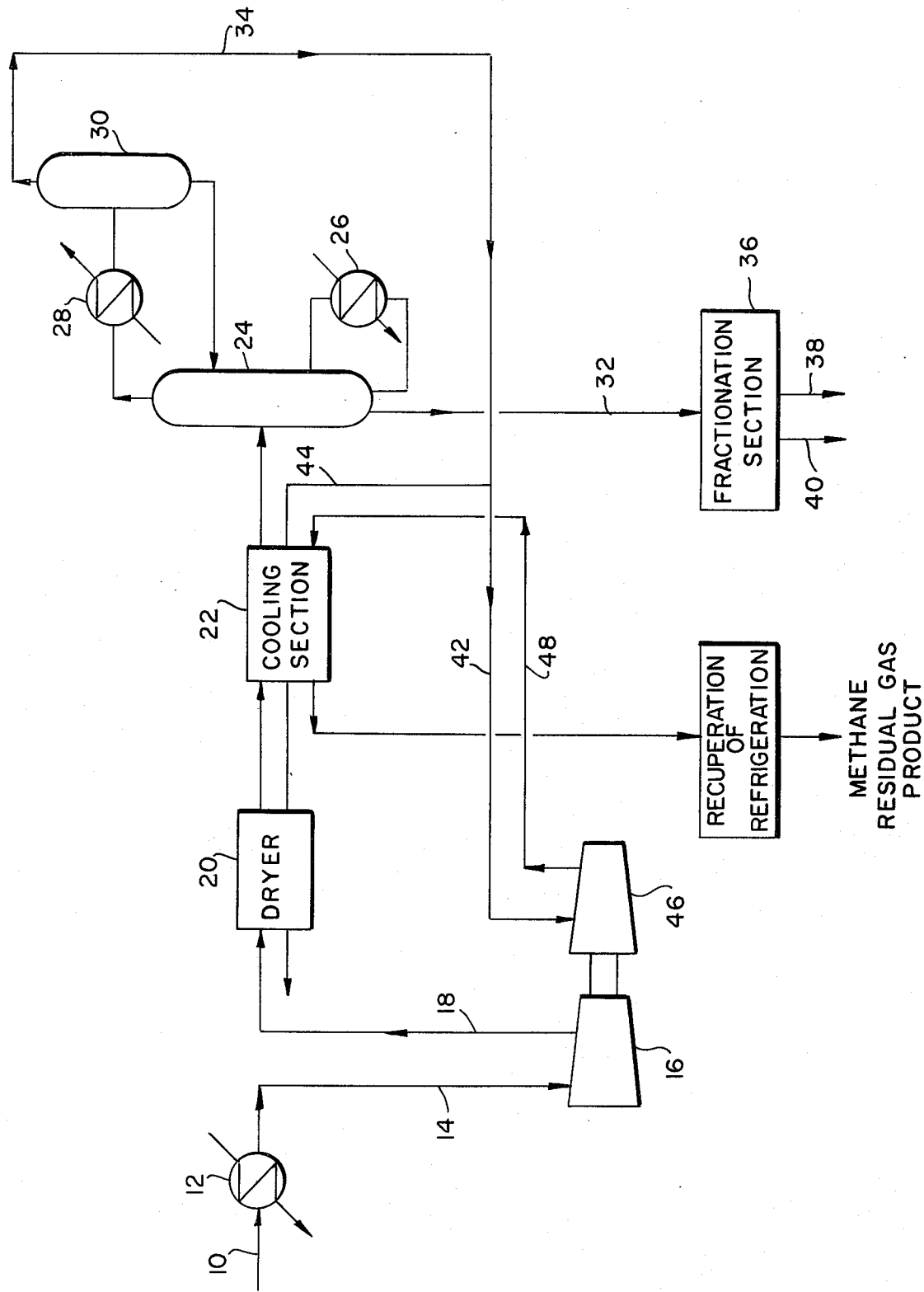

PROCESS AND APPARATUS FOR TREATING NATURAL GAS

BACKGROUND OF THE INVENTION

This invention relates to the treatment of natural gas, and more particularly, to the treatment of natural gas to recover $C_2+$ hydrocarbons.

Natural gas generally contains carbon dioxide, water vapor, ethane and heavier hydrocarbons, in addition to methane which comprises a major portion thereof. Ethane and the heavier hydrocarbons are generally extracted from natural gas streams, these streams are generally available at a pressure of from about 600 psig and above and often, it is necessary to send a residual methane gaseous stream at high pressure into a pipeline. When a high degree of hydrocarbon recovery is desired, a cryogenic process is invariably utilized requiring cooling and demethanization. Because of the thermodynamic properties of a natural gas stream, it is necessary to operate such a demethanizer at a pressure of from about 450 to 500 psia, which is substantially below the feed gas pressure and desired methane residual gas delivery pressure. Consequentially, the feed gas is depressurized and the methane residual gas is subsequently recompressed.

Heretofore, two basic processes have been employed for depressurizing the natural gas, i.e., (i) a Joule-Thomson throttling or (ii) an expansion through an expander. In the first mentioned process, the feed gas is chilled at high pressure and is then throttled through a valve. The methane residual gas is recompressed at least in part by a compressor driven by a steam turbine, electric motor or gas turbine. Such a process has several disadvantages, e.g., chilling of the natural gas is effected at high pressure and requires expensive, high pressure heat exchanges; the potential work of expansion is lost by throttling through a valve; and a special driver must be provided for the residual gas compressor.

The expansion processes either involve chilling in high pressure heat exchangers followed by expansion through a turboexpander, or expansion of the natural gas to the pressure of the demethanizer followed by chilling at the pressure of the demethanizer. Often, the expander is used to drive a compressor to partially recompress the methane residual gas. In both of such expander processes, an additional residual methane gas compressor including driver is usually required.

In many processes extracting ethane and heavier hydrocarbons, it is necessary to remove carbon dioxide from the natural gas feed to prevent freeze out of the carbon dioxide in the colder sections of the plant. This is generally effected by contacting the feed gas with an aqueous solution of an absorbent, such as monoethanolamine, and the like. Additionally, the natural gas feed has been passed through a drying step prior to introduction into the pipeline to thereby prevent hydrate formation in the pipeline. However, after contacting with an aqueous absorbent, further drying is required.

OBJECTS OF THE INVENTION

An object of the present invention is to provide a novel process and apparatus for treating natural gas to recover ethane and heavier hydrocarbons.

Another object of the present invention is to provide a novel process and apparatus for treating natural gas to recover ethane and heavier hydrocarbons obviating carbon dioxide removal facilities.

Still another object of the present invention is to provide a novel process and apparatus for treating natural gas to recover ethane and heavier hydrocarbons and to utilize work available from expansion of the feed stream to totally recompress a residual methane gaseous stream recovered from said treatment.

A still further object of the present invention is to provide a novel process and apparatus for treating natural gas to recover ethane and heavier hydrocarbons and to eliminate the requirement for externally powered booster compressors and associated drive assemblies to recompress a residual methane gaseous stream recovered from said treatment.

An additional object of the present invention is to provide a novel process and apparatus for treating natural gas to recover ethane and heavier hydrocarbons with a concomitant savings in power requirements.

Another object of the present invention is to provide a novel process and apparatus for treating natural gas to recover ethane and heavier hydrocarbons while minimizing water vapor removal facilities.

SUMMARY OF THE INVENTION

These and other objects of the present invention are achieved by heating the natural gas stream prior to the expansion and introduction into the demethanizer operating at low temperatures (generally between about 50° F. and − 150° F.) wherein ethane and heavier hydrocarbons are recovered. A residual gaseous methane stream is also recovered from the demethanizer and is recompressed, prior to the recovery of its cold potential, to a desired pipeline pressure by the work derived by expanding the heated natural gas stream.

BRIEF DESCRIPTION OF THE DRAWING

A more complete understanding of the present invention will become more apparent from the following description taken with the accompanying schematic flow diagram.

DESCRIPTION OF THE INVENTION

Referring to the drawing, natural gas, in line 10 at a pressure greater than the normal operating pressure (450 to 500 psia) of a demethanizer, is passed through a heat exchanger 12 wherein it is heated, such as by low pressure steam, to an elevated temperature. The heated natural gas in line 14 is passed through an expander 16 from which the expanded gas in line 18 is successively passed through drying and cooling sections 20 and 22, respectively, prior to introduction into a demethanizer 24. Since the temperature of the expanded natural gas leaving the expander 16 is relatively high and freezing is not yet a problem, the natural gas may be conveniently dried in a fixed bed. The cooling section 22 is conventional and includes heat exchange against boiling refrigerants such as propane and ethylene, and against streams recovered from the demethanizer tower 24, as more fully hereinafter described.

The demethanizer tower 24 is provided with a reboiler 26, a condenser 28, and a separator 30, and is operated in a manner known to those skilled in the art, at conditions to prevent freezing of $CO_2$. In the demethanizer tower 24, the expanded, dried and cooled natural gas stream is fractionated into a bottom stream in line 32 containing ethane and heavier hydrocarbons and some carbon dioxide, and into a gaseous overhead product in line 34 containing methane, nitrogen and carbon dioxide together with a small quantity of ethane. The tower bottoms in line 32 may be passed to a fractionation zone, generally indicated as 36, for separation into ethane in line 38 and heavier hydrocarbons in line 40. The gaseous overhead product in line 34 may contain of from about 50 to 95% of the carbon dioxide in the natural gas feed depending on the operation of the demethanizer 24.

The gaseous stream in line 34 is split into a major portion and a minor portion in lines 42 and 44, respectively. The minor portion in line 44 is passed in heat transfer relationship through the cooling section 22 to recover its refrigeration potential and is then used to regenerate the dessicant in dryer 20, on a once through basis, prior to being burned as fuel gas to satisfy the energy requirements of the plant. The major portion of the methane enriched gaseous stream in line 42 is recompressed prior to recovery of its cold potential, in a compressor 46 driven by expander 16 to a pressure sufficient for re-introduction into a pipeline (not shown) prior to recovery of the refrigeration potential in cooling section 22.

EXAMPLE OF THE INVENTION

Operation of the process and apparatus of the present invention is described in the following specific example which is intended to be merely illustrative and the invention is not to be limited thereto.

Natural gas in line 10 at a pressure of 725 psia, is heated to a temperature of about 115° F. in heat exchanger 12 by passage in indirect heat transfer relation with low pressure steam. The heated gaseous stream is thereafter expanded to approximately 500 psia in the turbo-expander 16 with a simultaneous reduction in temperature to about 75° F., at which temperature the natural gas may be conveniently dried in a dryer 20 of the fixed bed type.

The dried and expanded gas is cooled in the cooling section 24 to a temperature of −80° F. at a pressure of 490 psia. The demethanizer 24 is operated under conditions to provide an overhead product stream in line 34 which contains about 60–90%, preferably about 75% of the carbon dioxide in the feed while recovering 95% of the ethane in the natural gas as the tower bottom in line 32. About 4% of the residual methane stream in line 34 is passed by line 44 to regenerate the desiccant in the dryer and to provide the fuel gas requirements of the process. The major portion of the demethanizer overhead product in line 42 at a temperature of about −135° F. and at about 480 psia is recompressed, prior to reheating, to 725 psia totally by the expander 46 for introduction into the pipeline (not shown).

As hereinabove discussed, the process of the present invention eliminates the need of additional, external powered booster compressors and associated drive mechanisms to recompress the residual gaseous methane stream. By recompressing the demethanizer overhead at a temperature below that of the expander inlet temperature, the work required for recompression is balanced with that provided by expansion. Additionally, no carbon dioxide removal facilities are necessary for processing the feed gas since most of the carbon dioxide leaves the plant with the residual methane gas and only a minor portion with the ethane product. Although drying is required to achieve a low dew point necessary for low temperature processing, the drying system is substantially smaller than that for a natural gas stream saturated with moisture. When a natural gas stream is saturated with moisture because of an upstream carbon dioxide removal system, the plant fuel gas stream may be insufficient to satisfy dryer regeneration requirements on a once through basis thereby requiring a more costly regeneration gas recycle system including circulating compressors for desiccant regeneration should such a condition exist.

While the invention has been described in connection with several exemplary embodiments thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed:

1. A process for treating a gaseous natural gas stream including carbon dioxide and water vapor to recover ethane, which comprises:
    a. heating said gaseous natural gas stream;
    b. expanding said gaseous natural gas stream;
    c. passing said expanded natural gas stream through a drying section to remove water vapor;
    d. introducing into a demethanizer zone said dried and expanded natural gas stream of step (c) to separate a methane-enriched gaseous stream from an ethane-enriched stream;
    e. withdrawing said ethane-enriched stream from said demethanizer zone;
    f. withdrawing said methane-enriched gaseous stream from said demethanizer zone; and
    g. compressing at least a major portion of said methane-enriched stream to a delivery pressure by the work produced by expanding said gaseous natural gas stream.

2. The process as defined in claim 1 wherein said delivery pressure equals the pressure of said gaseous natural gas stream 3. The process as defined in claim 1 wherein said expanded gaseous natural gas is cooled prior to introduction into said demethanizer zone.

4. The process as defined in claim 3 wherein said expanded gaseous natural gas stream is at a pressure of between about 450 to 500 psia. prior to introduction into said demethanizer zone.

5. The process as defined in claim 4 wherein a major portion of said carbon dioxide in said gaseous natural gas stream is withdrawn from said dementhanizer zone in said methane-enriched gaseous stream.

6. The process as defined in claim 1 wherein a minor portion of said methane-enriched gaseous stream is passed in indirect contact with a heat transfer medium to recover the cold potential of said minor portion of said methane-enriched gaseous stream.

7. The process as defined in claim 6 wherein said minor portion of said methane-enriched gaseous stream is utilized to regenerate a desiccant utilized to remove water from said expanded natural gas stream.

8. The process as defined in claim 7 wherein said minor portion of said methane-enriched gaseous stream is utilized to provide the energy requirements of the process.

9. The process as defined in claim 1 wherein said expanded natural gas feed to said demethanizer zone is at a pressure of between about 450 to 500 psia.

10. An apparatus for treating a gaseous natural gas stream including water vapor to recover ethane and heavier hydrocarbon which comprises:
 a. means for heating said gaseous natural gas stream;
 b. expander means for reducing the pressure of said gaseous natural gas stream;
 c. drier means for removing water therefrom;
 d. a demethanizer for separating said expanded natural gas stream into a methane-enriched gaseous stream and an ethane-enriched stream; and
 e. compressor means for raising the pressure of said methane-enriched gaseous stream.

* * * * *